US 11,951,294 B2

(12) United States Patent
Baillie et al.

(10) Patent No.: US 11,951,294 B2
(45) Date of Patent: Apr. 9, 2024

(54) DEVICE FOR DISPENSING A FLUID PRODUCT

(71) Applicant: APTAR FRANCE SAS, Le Neubourg (FR)

(72) Inventors: Mickaël Baillie, Acquigny (FR); Maxime Huppé, Caudebec les Elbeuf (FR); Matthieu Norrant, Houlbec Cocherel (FR)

(73) Assignee: APTAR FRANCE SAS, Le Neubourg (FR)

( * ) Notice: Subject to any disclaimer, the term of this patent is extended or adjusted under 35 U.S.C. 154(b) by 25 days.

(21) Appl. No.: 17/786,323

(22) PCT Filed: Dec. 15, 2020

(86) PCT No.: PCT/FR2020/052458
§ 371 (c)(1),
(2) Date: Jun. 16, 2022

(87) PCT Pub. No.: WO2021/123613
PCT Pub. Date: Jun. 24, 2021

(65) Prior Publication Data
US 2023/0355897 A1    Nov. 9, 2023

(30) Foreign Application Priority Data
Dec. 19, 2019    (FR) ...................... 1915031

(51) Int. Cl.
*A61M 5/178*    (2006.01)
*A61M 5/50*    (2006.01)
*A61M 11/00*    (2006.01)

(52) U.S. Cl.
CPC ........ *A61M 5/5086* (2013.01); *A61M 11/007* (2014.02); *A61M 2205/13* (2013.01);
(Continued)

(58) Field of Classification Search
CPC ..................... A61M 11/007; A61M 11/02; A61M 15/0028; A61M 15/0036; A61M 15/004;
(Continued)

(56) References Cited

U.S. PATENT DOCUMENTS

2009/0128330 A1    5/2009    Monroe
2016/0193408 A1    7/2016    Schweikert et al.
(Continued)

FOREIGN PATENT DOCUMENTS

CN    102626533 A    8/2012
EP    0 546 607 A1    6/1993
(Continued)

OTHER PUBLICATIONS

Translation of International Preliminary Report on Patentability dated Oct. 29, 2021 from the International Bureau in International Application No. PCT/FR2020/052458.
(Continued)

*Primary Examiner* — Dionne Pendleton
(74) *Attorney, Agent, or Firm* — Sughrue Mion, PLLC

(57) ABSTRACT

Device for dispensing a fluid product having a body (1) and dispensing head (2) provided with a dispensing opening (3) and axially movable with respect to the body (1) during actuation. The body (1) accommodates a reservoir (10) containing one or two doses of fluid product. The device has an electronic module (100) with a wireless communication module (101), a geographical location module (102), and a power source (103). The device has a system of sensors (200, 201, 202) for detecting and signaling, automatically, an attempt to actuate the device, when a first sensor (200) is activated. The wireless communication module (101) is adapted to make an automatic emergency call to an emergency number when the sensor system detects an attempt to
(Continued)

Figure 1:
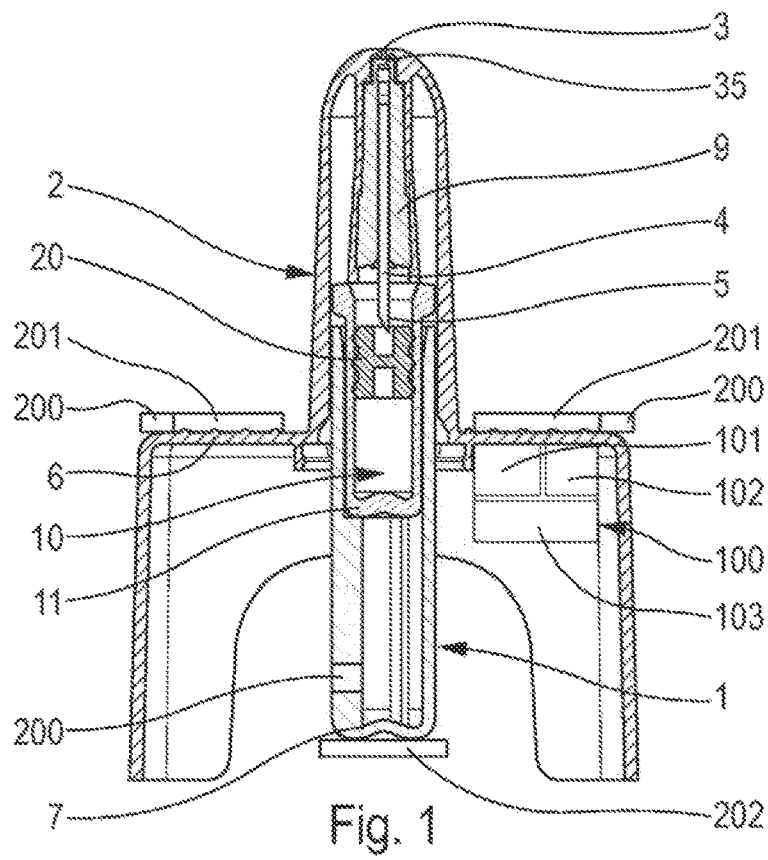

actuate the. The first sensor is activated when it detects an actuation force greater than 5N or 10N.

7 Claims, 1 Drawing Sheet

(52) U.S. Cl.
CPC . *A61M 2205/18* (2013.01); *A61M 2205/3306* (2013.01); *A61M 2205/3317* (2013.01); *A61M 2205/3368* (2013.01); *A61M 2205/3375* (2013.01); *A61M 2205/3592* (2013.01)

(58) Field of Classification Search
CPC .............. A61M 15/0043; A61M 15/08; A61M 2202/0468; A61M 2202/064; A61M 2205/13; A61M 2205/18; A61M 2205/3306; A61M 2205/3317; A61M 2205/332; A61M 2205/3368; A61M 2205/3375; A61M 2205/3553; A61M 2205/3592; A61M 2205/50; A61M 2205/8212; A61M 5/50; A61M 5/5086; A61M 3/00; A61M 5/00; B05B 11/02; G16H 20/13; G16H 40/63; G16H 40/67; G16H 20/17; A61B 5/7282; A61D 7/00
See application file for complete search history.

(56) References Cited

U.S. PATENT DOCUMENTS

| | | | |
|---|---|---|---|
| 2017/0257436 A1 | 9/2017 | Starr et al. | |
| 2021/0146061 A1* | 5/2021 | Byerly | A61M 5/31551 |
| 2021/0369971 A1* | 12/2021 | Katuin | A61M 5/31581 |
| 2022/0379013 A1* | 12/2022 | Kamen | G01F 11/08 |
| 2022/0387710 A1* | 12/2022 | Malloy | A61M 5/1723 |

FOREIGN PATENT DOCUMENTS

| | | |
|---|---|---|
| WO | 01/093926 A2 | 12/2001 |
| WO | 2008/091838 A2 | 7/2008 |
| WO | 2013/154954 A1 | 10/2013 |
| WO | 2016/097603 A1 | 6/2016 |

OTHER PUBLICATIONS

International Search Report for PCT/FR2020/052458 dated Mar. 30, 2021 [PCT/ISA/210].

* cited by examiner

DEVICE FOR DISPENSING A FLUID PRODUCT

CROSS REFERENCE TO RELATED APPLICATIONS

This application is a National Stage of International Application No. PCT/FR2020/052458 filed Dec. 15, 2020, claiming priority based on French Patent Application No. FR1915031 filed Dec. 19, 2019.

The present invention relates to fluid dispenser device, and more particularly to a device of the single-dose or two-dose type that is adapted to dispense one or two doses of fluid in a single actuation.

Devices of the single-dose or two-dose type are well-known. They generally comprise a reservoir containing one or two doses of fluid product, and a dispensing head provided with a dispensing opening, and which is axially movable with respect to said reservoir during actuation. Documents EP0546607 and WO2016097603 describe devices of this type.

For certain sensitive drugs, using the device and therefore dispensing a dose of the drug can indicate an emergency situation. For example, in the case of Naloxone-based drugs, which are in particular used to recover from an overdose (for drug addicts, but also for "normal" opioid users), the duration of activity of the drug is very limited, hence the necessity to rapidly consult a doctor or similar to obtain another dose once necessary. Another example relates to epinephrine, where it is also important that the patient goes rapidly to hospital for monitoring, as the effectiveness of epinephrine is only a few hours. This can be the same with other drugs, such as for example, Fentanyl.

Documents WO2008091838, US2016193408 and WO0193926 describe devices which detect the actuation of a device for dispensing drug, and which are capable of sending an alert, for example to an emergency call number. These devices allow to alert when the device is used, but if this use has been successful, and if the dose has been correctly dispensed, the alert to an emergency call number is, in reality, not useful. Such an alert is however highly desirable, if the user attempts to actuate the device, but is not successful in doing so, for example by lack of force, loss of knowledge, or malfunction of the device.

Documents CN102626533, WO2013154954, US2017257436 and US2009128330 describe other devices of the state of the art.

An object of the present invention is to provide a device for dispensing a fluid product, in particular of the single-dose or two-dose type, that does have the above-mentioned drawbacks.

The present invention also aims to provide a device for dispensing a fluid product, in particular of the single-dose or two-dose type, which automatically calls an emergency number during an attempt to actuate the device.

Another object of the present invention is to provide a device for dispensing a fluid product, in particular of the single-dose or two-dose type, that is simple and inexpensive to manufacture and to assemble.

The present invention therefore aims for a device for dispensing a fluid product comprising a body and a dispensing head provided with a dispensing opening and axially movable with respect to said body during actuation, said body accommodating a reservoir containing one or two doses of fluid product, said device comprising an electronic module which comprises a wireless communication module, such as a GSM module and/or a Wi-Fi module and/or a Bluetooth® module, a geographical location module, such as a GPS module and/or an antenna array, and a power source, such as a battery, said device comprising a sensor system for automatically detecting and signalling an attempt to actuate said device, said sensor system comprising at least a first sensor arranged on said dispensing head and/or on said body, said at least a first sensor being a pressure sensor, said sensor system detecting an attempt to actuate said device when said at least a first sensor is activated, said wireless communication module being adapted to make an automatic emergency call to an emergency number when said sensor system detects an attempt to actuate said device, wherein said at least a first sensor is activated when it detects either an actuation force greater than 5N, advantageously greater than 10N, or a pressure greater than 0.5 bar, advantageously greater than 1 bar.

Advantageously, said sensor system comprises at least one second sensor arranged on said dispensing head and at least a third sensor arranged on said body, to detect a controlling representative of an attempt to use said device when said second and third sensors are activated simultaneously.

Advantageously, said at least one second sensor is a microcurrent sensor, a capacitive sensor, an infrared sensor, a luminosity sensor, an audio sensor, a temperature sensor or a humidity sensor.

Advantageously, said at least a third sensor is a microcurrent sensor, a capacitive sensor, an infrared sensor, a luminosity sensor, an audio sensor, a temperature sensor or a humidity sensor.

Advantageously, before actuation, said electronic module is switched off or in standby mode, with a zero or minimum energy consumption.

Advantageously, said electronic module is switched on or awakened by said sensor system to go from its standby or switched off mode to an active mode.

Advantageously, said dispensing head comprises a radial flange and said body comprises a distal axial wall on which the user places their fingers during actuation, said at least a first sensor being arranged on said radial flange and/or on said distal axial wall.

Advantageously, said electronic module comprises timeout means to postpone the automatic emergency call by a few seconds from detecting an attempt to use by the sensor system.

According to a first advantageous variant, said fluid product is a liquid.

According to a second advantageous variant, said fluid product is a powder.

Advantageously, said reservoir contains one single dose of fluid product, dispensed in one single actuation.

In a variant, said reservoir contains two doses of fluid product, dispensed in two successive actuations.

Figure 2:
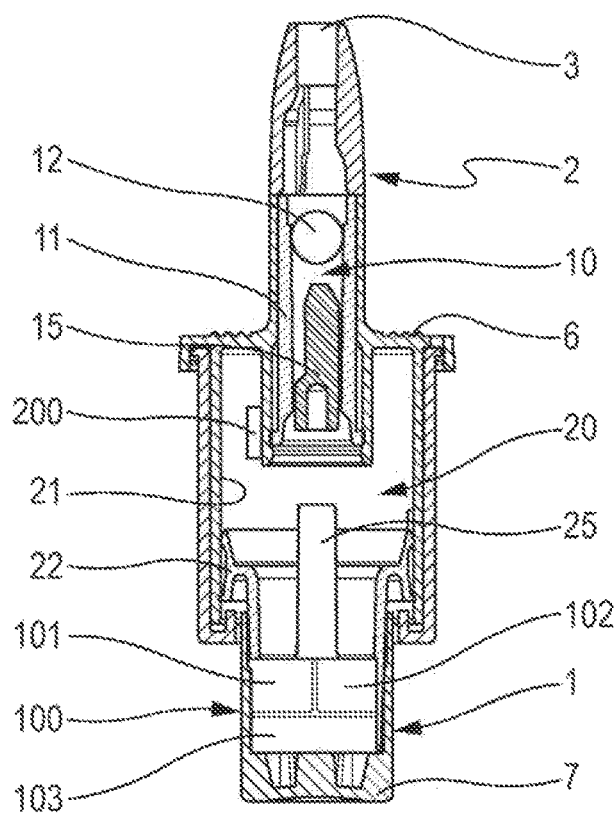

These and other characteristics and advantages will appear more clearly from the following detailed description made with reference to the accompanying drawings given by way of non-limiting examples, and wherein:

FIG. 1 is a schematic transverse cross-sectional view of a device of the single-dose type according to a first advantageous embodiment, in the rest position; and FIG. 2 is a schematic transverse cross-sectional view of a device of the single-dose type according to a second advantageous embodiment, in the rest position.

More specifically, the present invention relates to, on the one hand, a device of the single-dose type, such as for example, those disclosed in documents EP0546607 and WO02045866, and on the other hand, a device of the two-dose type, such as for example, that disclosed in document WO2016097603.

It is however understood that the present invention is not limited to these types of device, but is, however, applicable to all types of devices for dispensing fluid product, of the single-dose or two-dose type.

In the description, the terms "axial" and "radial" are relative to the longitudinal axis of the device. The terms "proximal" and "distal" are relative to the dispensing opening 3 formed in the dispensing head 2.

The invention applies, on the one hand, to devices of the single-dose type, such as those represented in the figures, in which all of the dose of fluid product contained in the device is dispensed in one single actuation of the device, and on the other hand, to devices of the two-dose type, in which the fluid product contained in the device is dispensed in two successive actuations of the device.

The device of the single-dose type represented in FIG. 1 comprises a body 1 which accommodates a reservoir 10 containing a dose of fluid product, generally a liquid, and a dispensing head 2, provided with a dispensing opening 3, which is axially movable with respect to said body 1 during actuation.

Advantageously, said reservoir 10 is formed by a blind hollow tube 11, e.g. made of glass, having a proximal axial opening 12 that is closed by a stopper 20, e.g. made of elastomer, that is adapted to slide in sealed manner into said tube 11 during actuation.

The dispensing head 2 generally includes a cannula or needle 4, of generally cylindrical shape that is connected at one end to said dispensing opening 3, and that is provided at its other end with a perforating tip 5 that is adapted to perforate said stopper 20 during actuation, the stopper 20 thus being moved in said reservoir 10 so as to expel the dose(s) of fluid product through said cannula 4 towards said dispensing opening 3. The cannula 4 may be inserted in a cannula support 9, that may itself be fastened in said dispensing head 2. Advantageously, a spray profile 35 may be formed directly upstream from the dispensing opening 3, e.g. between the bottom of said dispensing head 2 and the proximal axial end of said cannula support 9.

The dispensing head 2 comprises a radial flange 6 on which the use places one or more fingers during actuation.

FIG. 2 illustrates another type of device, in which the fluid product is a powder.

The device represented in FIG. 2 comprises a reservoir 10 containing one single dose of powder. A nasal dispensing head 2 is assembled on said reservoir 10, said head being intended to be inserted in a nostril of a user. Said nasal dispensing head 2 comprises a dispensing opening 3. The dispensing head 2 advantageously comprises a radial flange 6 forming a finger rest extending radially to facilitate actuation. The device further comprises an air discharge system 20 generating, during the actuation of said device, a flow of compressed air to dispense a dose of powder through said dispensing opening 3. Said air discharge system comprises an air chamber 21 and a piston 22 sealingly sliding in said air chamber 21 to compress the air contained in said air chamber 21 and thus generate said flow of compressed air. The piston 22 is preferably integral with a body 1 forming an actuation member on which the user will press during actuation to move the piston 22 in the air chamber 21. In the example represented in the figures, the reservoir 10 is formed by a hollow tube 11 open at its two axial ends, and closed at its proximal end by a closing element 12, such as a ball, and closed at its distal end by an insert 15. This insert 15 comprises an axial extension forming a rod, and can, upon actuation, slide in said hollow tube 11 to push said closing element 12 outside of its closing position. In this example, the piston 22 of the air discharge system 20 is rigidly connected to an axial projection 25 which extends in the proximal direction and which, during actuation, will move together with the piston 22 during the compression of the air contained in the air chamber 21. When said projection 25 of the piston 22 comes into contact with said insert 15 of the reservoir 10, a continuation of the movement of the piston 22 will cause the sliding of said insert 15 in said hollow tube 11 outside of its closing position. Said insert 15 will, on the one hand, open the passage between the air discharge system 20 and the reservoir 10 and, on the other hand, cause the expulsion of the closing element 12. Thus, the air compressed in the air chamber 21 will flow into said reservoir 10 and drive the dose of powder outside of said reservoir in the direction of said dispensing opening 3. Documents WO9946055, WO0245866, WO2015001281 and WO2017118827 describe devices of this type. Of course, other types of devices are also possible.

Typically, the actuation of the device in the two embodiments represented in the drawings is done by placing one or more fingers on said radial flange 6, and one finger, typically the thumb, on a distal axial wall 7 of the body 1, and by axially moving the body 1 with respect to the dispensing head 2.

The device moreover comprises an electronic module 100 connected to a sensor system 200, 201, 202.

The electronic module 100 advantageously comprises a wireless communication module 101, such as a GSM module, a geographical location module 102, such as a GPS module, and a power source 103, such as a battery.

At rest, the electronic module 100 is advantageously in standby mode, with a minimum energy consumption. In a variant, it could be completely switched off at rest, with therefore zero energy consumption. Awakening said electronic module is preferably done by the sensor system.

The sensor system comprises at least a first sensor 200 intended to detect an attempt to actuate. Thus, the present invention does not detect the actuation of the device, but any attempt to actuate, even unsuccessful.

Said at least a first sensor 200 is a pressure sensor, in particular a resistive force sensor (FSR sensor), of which the resistance varies according to the pressure which is applied to it.

In the example of FIG. 1, the actuation force of such a device is typically around 40N. The first sensor 200 aims to detect an attempt to actuate, therefore a force less than that necessary for the actuation.

In the example of FIG. 2, the actuation force of such a device is typically around 25N. The first sensor 200 aims to detect an attempt to actuate, therefore a force less than that necessary for the actuation.

Preferably, said at least a first sensor 200 is activated when it detects an actuation force greater than 5N, advantageously greater than 10N. This allows to avoid accounting for a simple controlling of the device, without any actual attempt to actuate.

In addition, in the example of FIG. 2, the air pressure in the air chamber 21 during actuation is typically around 1.5 bar.

In a variant, said at least a first sensor 200 is activated when it detects an air pressure greater than 0.5 bar, advantageously greater than 1 bar. This allows to avoid accounting for a simple controlling of the device, without any actual attempt to actuate.

Advantageously, the detection of an attempt to use is only validated if the sensor system detects the activation of a first sensor 200 for a predetermined minimum time, for example at least one second. This allows to remove furtive contacts not representative of a desire to use the device.

In the example of FIG. 1, the device comprises three first sensors 200, two on the radial flange 6 of the dispensing head and one on the body 1. In this variant, the first sensor(s) 200 detect(s) the pressure exerted by the fingers of the user on the device when they attempt to actuate the device.

Advantageously, the sensor system further comprises at least two other sensors 201, 202 intended to detect a controlling of the user representative of a clear desire to use the device. Thus, the present invention in addition detects an attempt to actuate the device, a controlling such as done when it is sought to actuate the device.

Advantageously, the sensor system comprises at least a second sensor 201, arranged on the radial flange 6 of the dispensing head 2 and at least a third sensor 202, arranged in the distal axial wall 7 of the body 1. These second and third sensors 201, 202 detect the fingers that the user places, on the one hand, on said radial flange 6, and on the other hand, on said distal axial wall 7 when they seek to actuate the device.

In the example represented, there are two second sensors 201, diametrically opposite on said radial flange 6, and one single third sensor 202 on said distal axial wall 7. Said second and third sensors 201, 202, according to their structure and their operation, can be fixed on the radial flange 6 and on the distal axial wall 7, as illustrated in FIG. 1, or inserted in said radial flange 6 and in said distal axial wall 7.

The association of at least a second sensor 201 on the radial flange 6 and of at least a third sensor 202 on the distal axial wall 7 allows to detect a controlling of the device which is representative of an attempt to use. Thus, if only one from among the second and the third sensor 201, 202 detects the presence of a finger but not the other sensor, then the alert is not generated. However, the activation of only one of the second and third sensors advantageously allows to "awaken" the electronic module 100, to make it go from its standby mode to its active mode.

When the second and third sensors 201, 202 are used, one single first sensor 200 can be sufficient for detecting a pressure during an attempt to actuate.

Several embodiment variants of the second and third sensors of the sensor system are possible.

According to a first variant, the second and third sensors 201, 202 are microcurrent sensors. In this first variant, each sensor comprises a positive pole and a negative pole, and a microcurrent is generated with a finger contacts the second sensor 201 and another finger contacts the third sensor 202.

In a variant, the second and third sensors 201, 202 are capacitive sensors. In this second variant also, a so-called "clamped" controlling is detected, with at least one finger on the second sensor 201 of the radial flange 6 and at least one finger on the third sensor 202 on the distal axial wall 7.

Also, according to other variants, the second and third sensors 201, 202 can be infrared sensors, luminosity sensors, audio sensors, temperature sensors or humidity sensors. Possibly, a combination of sensors is possible, the second sensor 201 not being necessarily identical to the third sensor 202.

In the example of FIG. 2, the device comprises one single first sensor 200, arranged in the air chamber 21.

In this variant, the first sensor 200 detects the air pressure in the air chamber 21 when the user attempts to actuate the device.

When the sensor system detects an attempt to actuate, the GPS module 102 will thus establish a geographical position of the device and the GSM module 101 will make an automatic emergency call to an emergency number, such as for example 110 in Europe, 15 or 18 in France, or 911 in the USA.

In an advantageous variant, the automatic emergency call is postponed by a few seconds from detecting an attempt to actuate by the sensor system, for example by timeout means provided in the electronic module 100. This implementation allows to deactivate the emergency call if, in this interval, the device is actually actuated by the user. In this event, the device would comprise a fourth sensor capable of detecting the actuation, for example the axial movement of the body 1 with respect to the dispensing head 2.

The automatic emergency call can comprise the transmission of a pre-recorded message accompanied by the geographical position determined by the GPS module 102. The call can also comprise a code for automatically identifying the drug arranged in the device for dispensing a fluid product. Advantageously, a coding could be provided for each sensitive drug to which the present invention applies more specifically. The call can also comprise an identification of the user, as well as time stamping.

In a variant, the call can put the user in contact with the emergency service, such that the user can directly communicate with said emergency service.

According to a first variant, the GSM module 101 can make emergency calls until the battery 103 is empty. According to a second variant, the call number can be predefined. According to a third variant, the device only makes one single call.

After the call(s), the electronic module 100 can return to standby mode or switch off.

The wireless communication module 101 could, in a variant, comprise a Wi-Fi module and/or a Bluetooth® module, and more generally, any type of wireless communication means using various bandwidths and/or frequencies.

The geographical location module 102 could, in a variant, comprise a Galileo module, and more generally any type of geographical location means. Thus, the geographical location module could not use satellite connection, but an antenna array, for example via a GSM or Wi-Fi or similar network. A combination of the two location means, by satellite and by antenna, can also be considered. The power source 103 could, in a variant, be made in the form of a rechargeable battery. Moreover, a condenser, or any similar means, can be associated with the power source 103 to allow to deliver, if needed, a high current to the different modules described above.

The present invention is described above with reference to several advantageous embodiments, but naturally any modification could be applied thereto by a person skilled in the art, without going beyond the scope of the present invention, as defined by the accompanying claims.

The invention claimed is:

1. A device for dispensing a fluid product comprising:
a body; and
a dispensing head provided with a dispensing opening and axially movable with respect to said body during actuation;
said body accommodating a reservoir containing one or two doses of fluid product;

said device comprising:
an electronic module which comprises:
a wireless communication module, such as a GSM module and/or a Wifi module and/or a Bluetooth® module;
a geographical locating module, such as a GPS module; and/or
an antenna array, and
a power source, such as a battery;
characterized in that said device comprises a sensor system for automatically detecting and signaling an attempt to actuate said device,
said sensor system comprising:
at least one first sensor disposed on said dispensing head and/or on said body,
said at least one first sensor being a pressure sensor, said sensor system detecting an attempt to actuate said device when said at least one first sensor is activated;
said wireless communication module being adapted to make an automatic emergency call to an emergency number when said sensor system detects an attempt to actuate said device;
wherein said at least one first sensor is activated when it detects either an actuating force greater than 5 Newton (N), an actuation force advantageously greater than 10 N, a pressure greater than 0.5 bar, or a pressure advantageously greater than 1 bar; and said sensor system comprising:
at least one second sensor arranged on said dispensing head and at least one third sensor arranged on said body, to detect a handling representative of an attempt to use said device when said second and third sensors are activated simultaneously.

2. Device according to claim 1, wherein said at least a second sensor is a microcurrent sensor, a capacitive sensor, an infrared sensor, a luminosity sensor, an audio sensor, a temperature sensor or a humidity sensor.

3. Device according to claim 1, wherein said at least a third sensor is a microcurrent sensor, a capacitive sensor, an infrared sensor, a luminosity sensor, an audio sensor, a temperature sensor or a humidity sensor.

4. Device according to claim 1, wherein said dispensing head comprises a radial flange and said body comprises a distal axial wall on which the user places their fingers during actuation, said at least a first sensor being arranged on said radial flange and/or on said distal axial wall.

5. Device according to claim 1, wherein said electronic module includes timeout means to postpone the automatic emergency call by a few seconds from detecting an attempt to use by the sensor system.

6. Device according to claim 1, wherein said reservoir contains one single dose of fluid product, dispensed in one single actuation.

7. Device according to claim 1, wherein said reservoir contains two doses of fluid product, dispensed in two successive actuations.

* * * * *